(12) United States Patent
Fujisato et al.

(10) Patent No.: US 7,910,360 B2
(45) Date of Patent: Mar. 22, 2011

(54) DEVICE AND METHOD FOR UNIFORMLY INOCULATING A SUBSTRATE HAVING THREE-DIMENSIONAL SURFACES

(75) Inventors: Toshiya Fujisato, Suita (JP); Takuro Kogoshi, Suita (JP); Yusuke Suga, Suita (JP); Akio Kishida, Suita (JP); Takeshi Nakatani, Suita (JP); Soichiro Kitamura, Suita (JP)

(73) Assignees: JAPAN as represented by PRESIDENT OF NATIONAL CARDIOVASCULAR CENTER, Osaka (JP); Nipro Corporation, Osaka (JP)

( * ) Notice: Subject to any disclaimer, the term of this patent is extended or adjusted under 35 U.S.C. 154(b) by 1138 days.

(21) Appl. No.: 10/568,701

(22) PCT Filed: Aug. 18, 2004

(86) PCT No.: PCT/JP2004/011817
§ 371 (c)(1),
(2), (4) Date: Dec. 8, 2006

(87) PCT Pub. No.: WO2005/017092
PCT Pub. Date: Feb. 24, 2005

(65) Prior Publication Data
US 2007/0166818 A1    Jul. 19, 2007

(30) Foreign Application Priority Data

Aug. 19, 2003 (JP) ................ 2003-294766

(51) Int. Cl.
*C12M 1/10* (2006.01)
*C12M 3/02* (2006.01)
(52) U.S. Cl. .................. 435/298.2; 435/303.3; 366/217
(58) Field of Classification Search ............. 435/298.2
See application file for complete search history.

(56) References Cited

U.S. PATENT DOCUMENTS
5,266,273 A * 11/1993 Coombs ............. 422/101

FOREIGN PATENT DOCUMENTS
| JP | 2002-045173 | 2/2002 |
| JP | 2003-009852 | 1/2003 |
| JP | 2003-070485 | 3/2003 |

* cited by examiner

*Primary Examiner* — William H Beisner
(74) *Attorney, Agent, or Firm* — Millen, White, Zelano & Branigan, P.C.

(57) ABSTRACT

An apparatus and method for inoculating a biological substrate with cells include provision for rotating a container in which the substrate and a cell suspension are received about first and second axes of rotation. The apparatus comprises said container, first drive means for rotatably supporting the container about the first axis, and second drive means for rotatably supporting the first drive means about the second axis. The first and second axes of rotation do not lie in the same plane and extend in different directions so that the container revolves around the second axis while the container is rotating about the first axis. The inoculation method utilizes this apparatus.

18 Claims, 6 Drawing Sheets

SIDE            BOTTOM

FIG. 7

VESSEL WALL

SURFACE OF HEART
VALVE LEAFLET

DEVICE AND METHOD FOR UNIFORMLY INOCULATING A SUBSTRATE HAVING THREE-DIMENSIONAL SURFACES

FIELD OF THE INVENTION

This invention relates to an apparatus and method for performing uniform inoculation of a substrate three-dimensional surfaces with cells. The apparatus and method rotate a container containing the substrate and a cell suspension about mutually different axes lying in mutually different planes simultaneously.

BACKGROUND PRIOR ART

JP 2000-316899A discloses an apparatus and method for culturing adherent cells on a substrate having uneven three-dimensional surfaces wherein a cell suspension is placed in a container containing the substrate, and the cells are cultured on the substrate while rotating the container about plural axes.

In such apparatus, the plural rotational axes of the container intersect with each other to create a quasi-gravity free state in the container so that the cell suspension in the vicinity of the substrate is not fully flowing to uniformly convey cells throughout the substrate surfaces. This results in uneven distribution of cells and adversely affect the quality of cell suspension.

Another problem of the known tissue culture apparatus is associated with coaxial placement of the drive shaft of each drive means for rotating the culture container with each rotational axis of the container. This not only makes the design of the apparatus complicated and costly but makes the container not easily accessible.

In order to eliminate or ameliorate the above problems, JP 2005-45173A and JP 2003-70458 disclose a similar apparatus and method wherein the cell suspension is positively circulated through the rotating culture container from an external source. The apparatus is still complicated in design and coupling and decoupling of a conduit for circulating the cell suspension is not easily performed.

DISCLOSURE OF THE INVENTION

An object of the present invention is to provide an apparatus and method for inoculating a biological substrate with seed cells. The apparatus comprises a container for receiving a biological substrate and a cell suspension therein, first drive means for rotatably supporting said container about a first rotational axis, and second drive means for rotatably supporting said first drive means about a second rotational axis whereby revolving said container around said second rotational axis while rotating said container about said first rotational axis, wherein the first and second rotational axes lie in mutually spaced apart two planes and extend in different directions in said planes. Thus, a gravity field is created in the cell suspension in the container to assist self-dispersion of cells by providing the container with an offset motion relative to its center.

Another object of the present invention is to provide an apparatus and method for inoculating a biological substrate with cells which is relatively simple in design and less costly and which allows easy access to the container.

In order to accomplish the above and other objects, the apparatus of the present invention comprises a container for receiving a biological substrate and a cell suspension therein, first drive means for rotatably supporting said container about a first rotational axis, and second drive means for rotatably supporting said first drive means about a second rotational axis to provide said rotating container with a revolutional movement around the second rotational axis, wherein the first and second rotational axes lie in mutually different spaced apart planes and extend in different directions in said planes.

At least one of the first and second rotational axes is offset relative to the drive shaft of the associated drive means. Thus, the first and second rotational axes are neither parallel nor intersecting with each other and extend in different directions.

As a result of placement of the first and second rotational axes as above, the culture container revolves around the second rotational axis while rotating about the first axis. The resulting combined motion of the container creates a gravity field in the cell suspension to assist self-dispersion of cells.

In a preferred embodiment, the first and second rotational axes may extend in angularly spaced apart directions defining approximately 90° about a center line that intersects parpendicularly with both rotational axes. This arrangement assists effective distribution and seeding for a substrate having uneven three-dimensional surfaces.

As described above, at least one of first and second rotational axes is offset relative to the drive shaft of respective drive means. This arrangement eliminates need for coaxial placement of the drive shaft and drive source with the rotational axis and allows simplified and less costly design for the apparatus as well as easy access to the container.

Particularly, the above arrangement can avoid the drive shaft of the first drive means from interfering with loading and unloading of the culture container to and from the first drive means for rotatably supporting the culture container.

Similarly, the above arrangement also facilitates loading and unloading of the first drive means to and from the second drive means for rotatably supporting the first drive means which, in turn, facilitates loading and unloading of the culture container.

Since the apparatus is configured to allow removal of the container without breaking closed sterile condition, the container containing inoculated substrate may be transferred to an incubator for further growth of cells while maintaining the sterility.

In another preferred embodiment, the rotational drive of the container and/or the first drive means is accomplished using frictional power transmission means.

The frictional power transmission not only reduces the number of parts otherwise required for transmitting driving force to the container to simplify the design of the apparatus but also facilitates loading and unloading of the container to and from the first drive means as well as loading and unloading of the first drive means to and from the second drive means.

It should be noted, however, that the present invention is not limited to the use of frictional power transmission means but includes other conventional power transmission means such as gears, belt/pulley and the like.

In a further embodiment, the first and second drive means are controllable independently from each other by having their own controllers.

Independent control of the first and second drive means allows to vary the three-dimensional movement of the container for adapting the movement to the geometry of a particular substrate when the substrate and the cell suspension are present in the container.

The independent control of the first and second drive means enables both removable support of the container on the first drive means and removable support of the first drive means on the second drive means.

Thus, the first and second drive means are independent and separable from each other. Therefore, the first rotational axis about which the container rotates and the second rotational axis about which the first drive means rotates may be set variably in their absolute and relative positions.

Consequently, the apparatus of the present invention can impart the container with offset rotation/revolution relative to the gravity center of container to create a gravity field for assisting self-suspension and resuspension of cells.

BEST MODE FOR CARRYING OUT OF THE INVENTION

Now the apparatus and method for inoculating a substrate with cells will be described in detail by making reference to the accompanying drawings.

Figure 1:
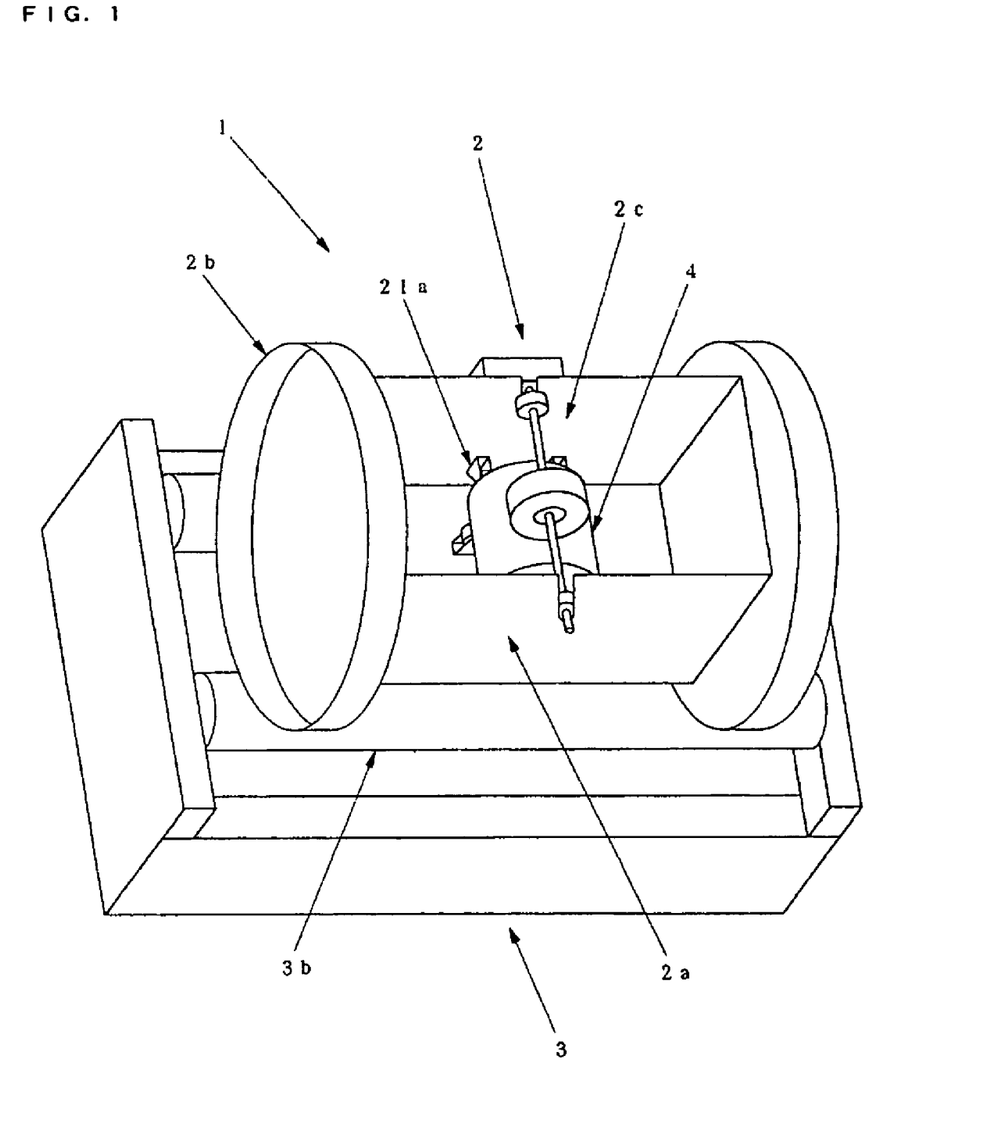
FIG. 1 is a schematic view of the entire apparatus of the present invention for inoculating a substrate with cells.

The inoculation apparatus 1 according to the present invention is illustrated schematically in FIG. 1.

Figure 2:
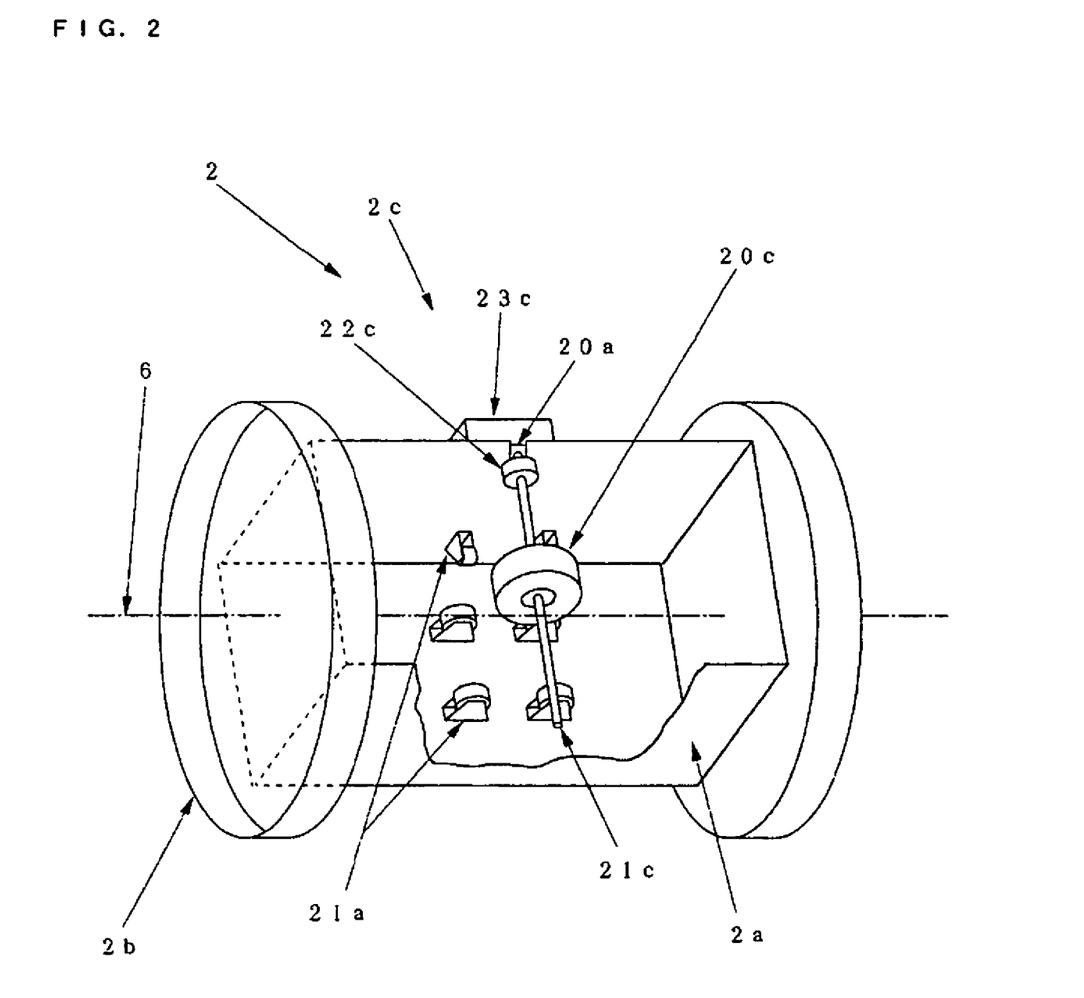
FIG. 2 is a schematic view of the first rotational drive means of the apparatus of FIG. 1.

The apparatus 1 of the present invention comprises a culture container 4 for receiving a biological substrate 40b and a cell suspension 40c (see, FIG. 4), first rotational drive means 2 for rotatably supporting the container 4 about a first rotational axis 5 (see, FIG. 4), and second rotational drive means 6 for rotatably supporting the first drive means 2 about a second rotational axis 6 (see, FIG. 2).

Figure 4:
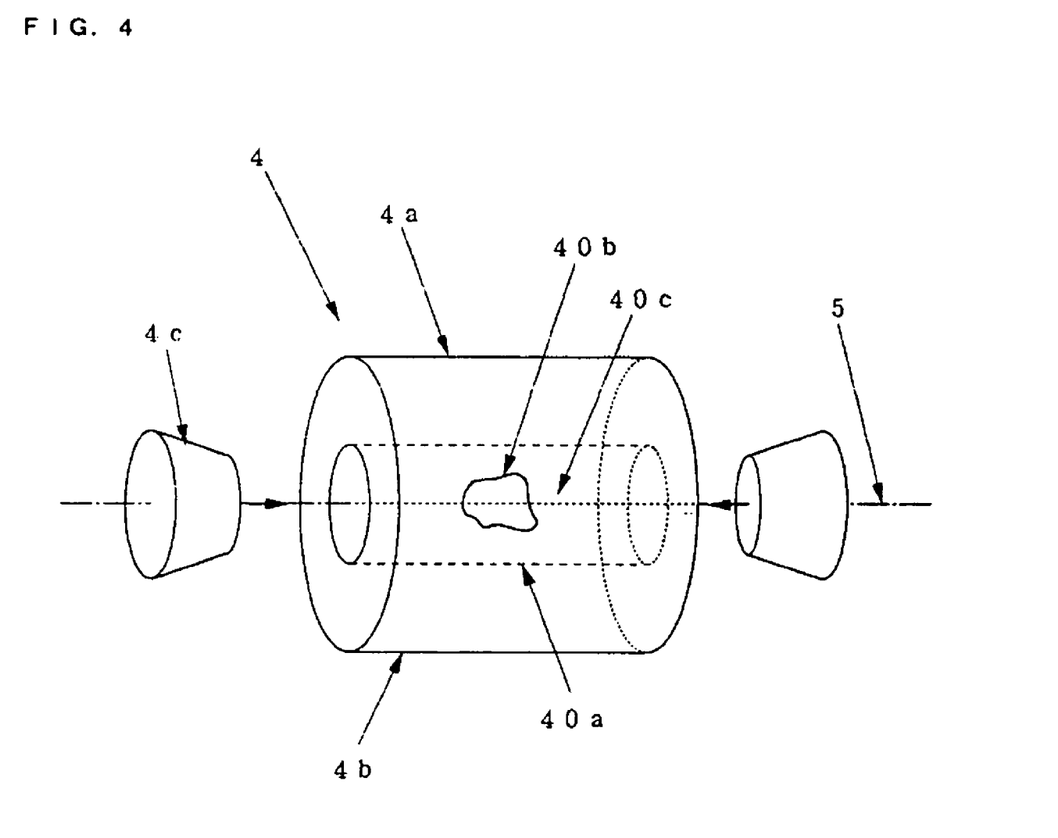
FIG. 4 is a schematic view of the culture container of the apparatus of FIG. 1.

The first and second rotational axes 5 and 6 are set to extend in mutually different spaced apart planes in different directions. Namely, the first and second rotational axes 5 and 6 are neither parallel nor intersecting with each other.

Since the first and second rotational axes 5 and 6 of the apparatus may be set variably in their absolute and relative positions, the rotational axes 5 and 6 may also lie in the same plane and intersect with each other if so desired.

The positioning the first and second rotational axes in mutually different planes results in a revolutional orbital movement of the rotating container 4 around the second rotational axis 6. When the gravity center of the container 4 is offset from the first rotational axis 5 during rotation of the first drive means about the second rotational axis, then a gravity field is created in the cell suspension 40*c* in the container 4 to assist self-suspension of cells.

For those substrates 40*b* having uneven or complicated surfaces in particular, it is preferrable and effective to angularly space apart the first and second rotational axes to define 90° about a line which vertically and parpendicularly intersects both the first and second rotational axes.

In the illustrated embodiment, the container 4 is rotated about the first rotational axis 5 by means of a frictional power transmission mechanism comprising a rotatable wheel 20*c* and the cylindrical wall 4*b* of the container 4. The rotatable wheel 20*c* is rotated, in turn, by a electric motor (not shown) housed in a drive unit 23*c* in the first drive means 2 via a drive shaft to which the wheel 20*c* is secured.

In the illustrated embodiment, the first drive means 2 is also rotated about the second rotational axis 6 by means of a frictional power transmission mechanism comprising, in this case, a pair of rotable wheels 2*b* for securely supporting the housing 2*a* of the first drive means 2 therebetween, and a pair of rotatable rolls 3*b* which rotatably support the pair of rotatable wheels 2*b* therebetween. At least one of the rotatable rolls 3*b* is rotated, in turn, by an electric motor (not shown).

The above drive mechanism utilizing frictional power transmission is simpler in structure than the drive mechanism utilized in the prior art for rotating the culture container because it includes less number of components otherwise needed for transmitting driving force to the container such as gears, belts and pulleys and the like. This drive mechanism also allows easy loading and unloading of the container 4 to and from the first drive means 2 without breaking the sterility within the container and loading and unloading of the first drive means 2 to and from the second drive means 3.

Is should be noted, however, that the present invention is not limited to the above drive mechanism and other drive mechanisms including gears, belts and pulleys and the like may also be utilized.

For instance, rotatable wheels 2*b* and rotatable rolls 3*b* can have meshing gear teeth, respectively to transmit rotation of the rolls 3*b* to the wheels 2*b*.

As described above, the first and second rotational axes 5 and 6 are not in alignment with the drive shaft for rotating the container 4 and the drive shaft for rotating the first drive means 2, respectively. In other words, the axis of wheel 20*c* and the axis of one of rolls 3*b* are offset from the first and second rotational axes 5 and 6, respectively. These arrangements not only enable the entire apparatus to be simpler and less costly in construction but provide easy access to the container 4 and the first drive means 2.

In particular, such an arrangement of the first and second axes 5, 6 and the associated drive shafts allows loading and unloading of the container 4 to and from the first drive means 2 without interference by the drive shaft for rotating the container. As a result, the container 4 becomes accessible more easily.

Similarly, since the first drive means 2 is removably supported on the second drive means 3, one can easily load and unload the first drive means 2 to and from the second drive means 3 and then load and unload the container 4 to and from the first drive means 2.

FIG. 2 is a schematic view of the first drive means 2 with the container 4 being removed.

The first drive means 2 comprises a housing 2*a* for rotatably supporting the container 4 and a drive mechanism 2*c* for rotating the container 4 about the first rotational axis 5. A pair of rotatable wheels 2*b* are secured to opposing end walls of the housing 2*a* coaxially with the second rotational axis 6.

In the illustrated embodiment, the housing 2*a* has a box shape and includes a pair of side walls, a pair of end walls and a bottom wall taking durabily, weight and easy access to the container 4 into consideration. However, the housing 2*a* may have any shape or configuration other than the shape shown in FIG. 2 provided it can support the container 4, a pair of rotatable wheels 2*b* and the drive mechanism 2*c*.

The housing 2*a* includes a cutoff portion or slot 20*a* in the top of each side wall for mounting the drive mechanism 2*c* inside and outside the side walls.

The container 4 is rotatably and removably mounted on a plurality of support rollers 21*a* disposed in rows in the interior of the housing 2a and can rotate on the support rolls 21a about the first rotational axis 5 as shown in FIGS. 1 and 4.

The drive mechanism 2c for rotating the container 4 about the first rotational axis 5 comprises a drive shaft 21c, a drive wheel or roller 20c coaxially attached to the drive shaft 21c, a pair of bearings 22c attached to the housing 2a for rotatably supporting the drive shaft 21c, and a drive unit 23c for driving the shaft 21c.

The drive unit 23c includes self-contained electric motor, battery and controller (not shown) and, therefore, can operate without need for external power supply.

The first drive means 2 thus have no external wiring and, therefore, may be controlled in operation including start and stop of rotation of the container independently from the operation of the second drive device 3.

In the illustrate embodiment, the drive unit 23c may be attached and fixed to the housing 20a by inserting the drive shaft 21c carrying the unit 23c at one free end thereof into the cutout portion or slot 20a. The attachment of the drive mechanism 2c to the housing 2a in this manner allows to adjust the distance between the periphery of the drive roller 20c and the outer surface of cylindrical container tube 4 or hollow cylinder 4b surrounding the container 4 to adapt the drive mechanism 2c for various size or diameter of the container or cylinder. Thus steady and resilient friction contact may be established between the drive roller 20c and the container cylinder 4b.

In the embodiment shown in FIG. 2, the culture container 4 may be set in the first drive device 2 as follows. The container 4 or cylinder 4b surrounding the container is placed between the rows of support rollers 20c in position. Then the drive roller 20c is lowered until it contact with the container 4 or cylinder 4b before a pair of bearings 22c are fastened using suitable means on the side walls of the housing 2a while slightly pushing the drive roller 20c against the container 4 or cylinder 4b.

The container 4 may be removed from the first drive means 2 for access by reversing the above procedure.

Figure 3:
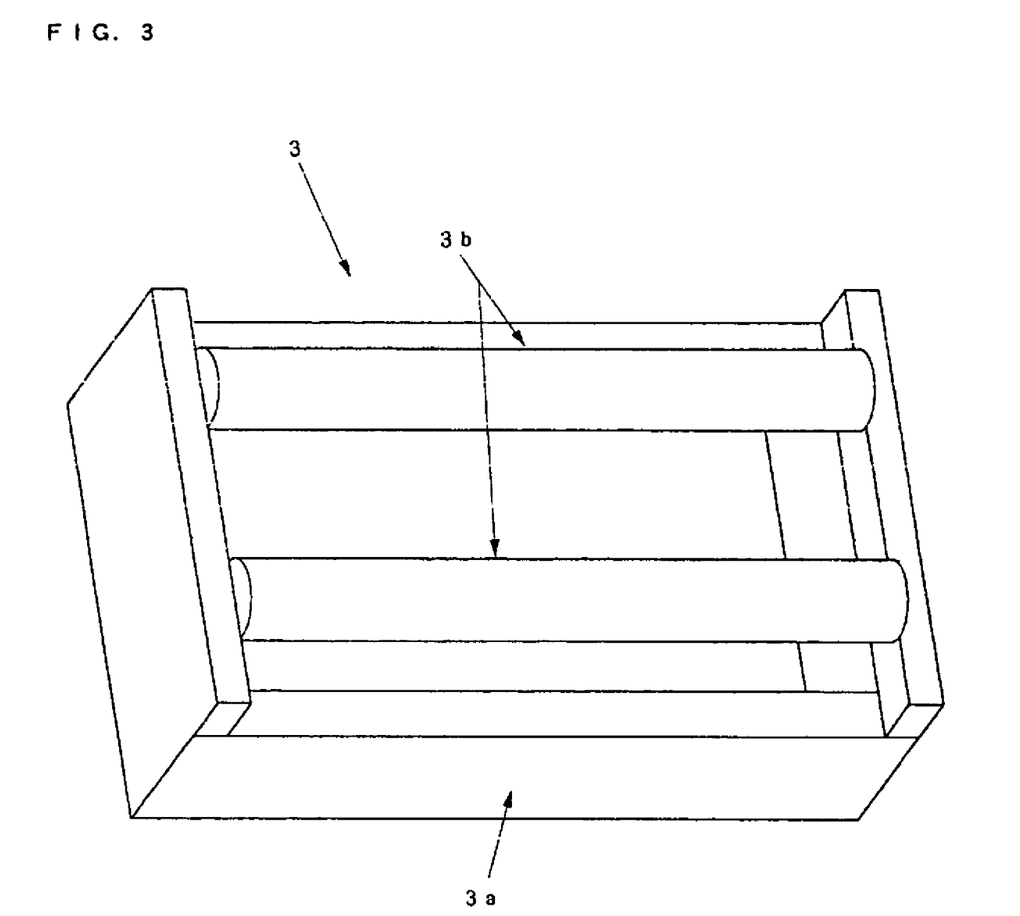
FIG. 3 is a schematic view of the second rotational means of the apparatus of FIG. 1.

FIG. 3 shows schematically the second drive means 3 of the apparatus of the present invention with the first drive means 2 being removed therefrom.

The second drive means 3 comprises a pair of elongate drive rolls 3b disposed in parallel for rotatably supporting the first drive means 2 therebetween and a base or frame member 3a for rotatably mounting the pair of drive rolls 3b. The base or frame member 3a also includes an electric motor and a controller for the motor (not shown) for rotating at least one of the pair of drive rolls 3b.

The second drive means 3 is not limited to the embodiment as shown and commercially available devices may be employed provided they can rotatably support a pair of wheels 2b of the first drive means 2 between a pair of parallel rolls.

Turning to FIG. 4, an embodiment of the culture container used in the apparatus of the present invention is shown schematically.

In the illustrated embodiment, the culture container 4 comprises a hollow cylindrical body 4a defining a chamber 40a, a cylindrical sleeve 4b fitted over the outer surface of the cylindrical body, and a pair of plugs 4c for closing the open ends of the chamber 40a. The plugs 4c are fitted in the open ends after a substrate 40b and a cell suspension 40c are placed in the chamber 40a.

The cylindrical sleeve 4b shown in FIG. 4 is used for providing the body 4a with a cylindrical outer surface when the body 4a does not have a cylindrical outer surface.

When the container itself is not cylindrical body suitable to be rotationally driven by the drive wheel 20c of the first drive means, the sleeve 4b surrounding the container body 4a is mounted between the drive wheel 20c and the supporting rollers 21a in friction contact.

However, the container 4 is not limited to the particular embodiment shown in the drawing. For example, the sleeve 4b and the container body 4a may be fabricated as an integral component defining a cylindrical our surface suitable for being driven by the drive wheel 20c.

Preferably, the container 4 is entirely fabricated from transparent material such as transparent plastics or glass for viewing the contents thereof.

The present invention thus provides an apparatus and method which enables a substrate 4b having uneven or complicated surfaces to be inoculated or seeded uniformly by rotating a culture container 4 containing the substrate and the cell suspension simultaneously about two different axes 5 and 6 lying two different planes, respectively. Examples of the target substrates include tissues of human and other mammalian origin, tissues of vertebrates origin including fishes, birds, amphibians or reptiles, plant tissues and synthetic tissues. Human, porcine and bovine tissues are typical.

As will be appreciated from the above description, the first and second drive means 2 and 3 are separated and operate independently from each other. Consequently, the absolute and relative positions of the first and second rotation axes 5 and 6 of the container 4, namely the spacing between these axes may be adjusted as desired by, for instance, changing the radius of rotation of the container sleeve 4b and the wheels 2b attached to the first drive means 2 so as to be driven by the second drive means 3.

Thus, the container 4 turns in orbital motion around the second rotational axis 6 while rotating about the first rotational axis 5. Furthermore, the gravity center of the container 4 is always offset from the first rotational axis 5 and also from the orbit around the second rotational axis 6 during the rotation and revolution. As a consequence of combined motions of the container, a fixed gravity field is not created in the container 4 as opposed to the gyratory culture.

In addition, the entire apparatus becomes simpler and less costly in construction while allowing easy access to the container 4 by placing at least one of the first and second axes 5 and 6 in an offset position from the drive mechanism thereof.

The following Example demonstrates the experimental cell culture using the apparatus of the present invention.

EXAMPLE 1

Figure 5:
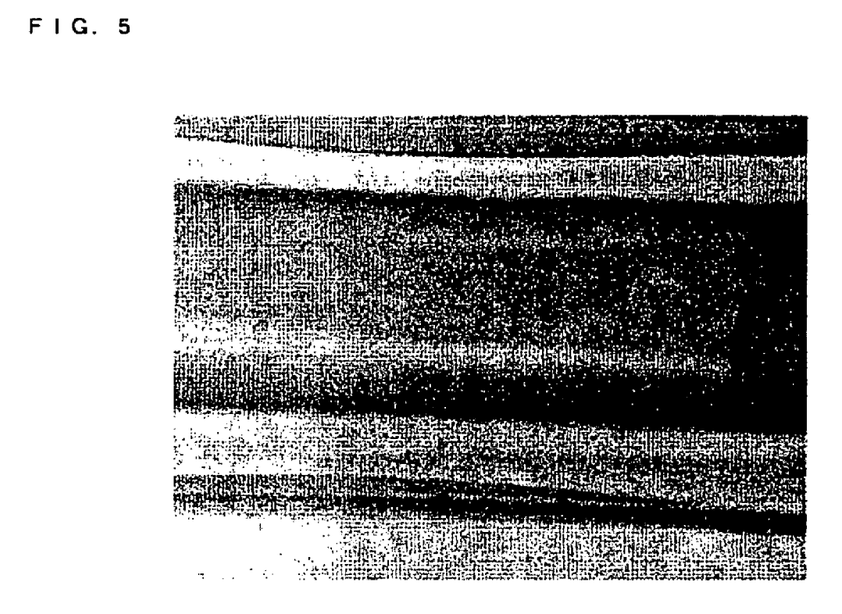
FIG. 5 is a photograph showing the result of Example 1 of the method of the invention.

A volume of vascular endothelium cell suspension 40c was sealed in a cylindrical glass container 4 defining a chamber having an inner diameter of 3 mm. The glass container 4 was rotated at 12 rpm in the first drive means 2 about the first rotational axis 5 in the first drive means 2 while rotating the first drive means 2 at 4 rpm about the second rotational axis on the second drive means 3 for 2 hours. The cells were sedimented on the wall of the container 4 forming a substantially uniform layer as shown in FIG. 5.

EXAMPLE 2

Figure 6:
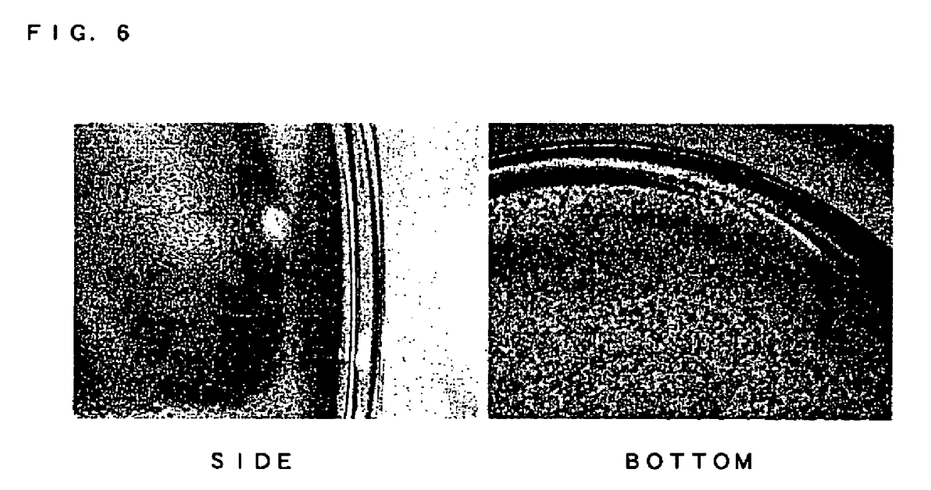
FIG. 6 is a photograph showing the result of Example 2 of the method of the present invention.

A volume of a suspension of vascular endothelium cells was sealed in a cylindrical glass container defining a chamber having an inner diameter of 1 cm. The glass container 4 was rotated at 12 rpm about the first rotational axis 5 in the first drive means 2 while rotating the first drive means 2 at 4 rpm about the second rotational axis 6 on the second drive means 3 for 2 hours. The cells were sedimented on the side and bottom surfaces uniformly as shown in FIG. 6.

Figure 7:
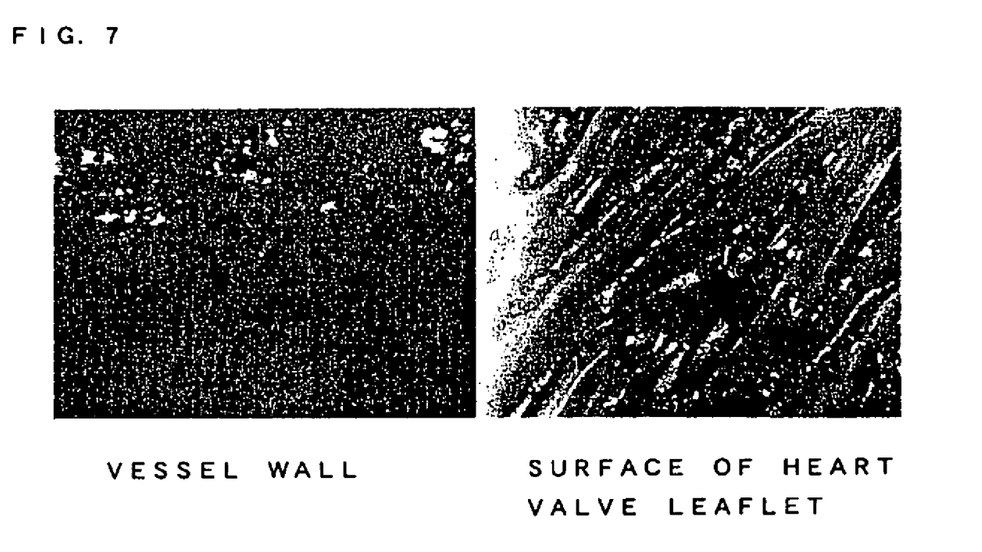
FIG. 7 is a photograph showing the result of Example 3 of the method of the present invention.

A segment of decellularized porcine heart valve tissue and a volume of a suspension of vascular endothelium cells were sealed in a similar container 4 as used in the preceding Examples. The container 4 was rotated at 12 rpm about the first rotational axis 5 in the first drive means 2 while rotating the first drive means at 4 rpm at 4 rpm about the second rotational axis 5 for 2 hours. The cells were sedimented and grown substantially uniformly on the blood vessel walls and the leaflet walls of the heart valve as shown in FIG. 7.

The invention claimed is:

1. An apparatus for inoculating a biological substrate with cells comprising:
    a container for receiving said substrate and a suspension of said cells;
    first drive adapted for rotatably supporting said container for rotation through 360° about a first rotational axis extending through said container; and
    second drive adapted for rotatably supporting said first drive for rotation through 360° about a second rotational axis whereby said container revolves continuously around said second rotational axis while said container is rotating about said first axis;
    wherein said first and second rotational axes lie in mutually spaced apart planes and extend in different directions in said planes.

2. The apparatus according to claim 1, wherein said first and second axes extend neither in parallel nor intersecting with each other.

3. The apparatus according to claim 1 wherein said first and second rotational axes extend in angularly spaced apart directions defining approximately 90° about a center line that intersects perpendicularly both said first and second rotational axes.

4. The apparatus according to claim 1 wherein at least one of said first and second rotational axes is offset from the drive shaft of a mechanism for rotating said container or said first drive.

5. The apparatus according to claim 1 wherein said container is removably mounted in said first drive.

6. The apparatus according to claim 1 wherein said first drive is removably mounted in said second drive.

7. The apparatus according to claim 1 wherein said first and second drive include their own control for controlling the rotation of said container and said first drive independently from the other control.

8. The apparatus according to claim 1 wherein said first drive transmit a driving force to said container via frictional contact between them.

9. The apparatus according to claim 1 wherein said second drive transmit a driving force to said first drive via frictional contact between them.

10. A method for inoculating a biological substrate with cells by an apparatus according to claim 1, comprising
    receiving said substrate and a suspension of said cells in a container;
    rotatably supporting said container in the first drive for rotation through 360° about the first rotational axis extending through said container;
    rotating said container about said first rotational axis and said first drive through 360° about said second rotational axis whereby said container revolves continuously about said second rotational axis while said container is rotating about said first rotational axis;
    wherein said first and second rotational axes lie in mutually spaced apart planes and extend in different directions in said planes.

11. The method according to claim 10 wherein said first and second rotational axes extend in angularly spaced apart directions defining approximately 90° about a center line that intersects perpendicularly both said first and second rotational axes.

12. The method according to claim 10 wherein at least one of said first and second rotational axes is offset from the drive shaft of a drive mechanism for rotating said container or said first drive.

13. The method according to claim 10 wherein said container is removably mounted in said first drive.

14. The method according to claim 10 wherein said first drive is removably mounted in said second drive.

15. The method according to claim 10 wherein said first and second drive include their own control for controlling the rotation of said container and said first drive independently from the other control.

16. The method according to claim 10 wherein said first drive transmit a driving force to said container via frictional contact between them.

17. The method according to claim 10 wherein said second drive transmit a driving force to said first drive via frictional contact between them.

18. A method for inoculating a biological substrate with cells by an apparatus according to claim 1, comprising
    receiving said substrate and a suspension of said cells in a container;
    rotatably supporting said container in the first drive for rotation through 360° about the first rotational axis extending through said container;
    rotatably supporting said first drive in the second drive for rotation about the second rotational axis;
    rotating said container about said first rotational axis and said first drive through 360° about said second rotational axis whereby said container revolves continuously around said second rotational axis while said container is rotating about said first rotational axis;
    wherein said first and second rotational axes extend neither in parallel nor intersecting with each other.

* * * * *